United States Patent [19]
Evans

[11] Patent Number: 5,514,828
[45] Date of Patent: May 7, 1996

[54] PROCESS FOR POLYMERIZING POLYFLUOROALKYLSILOXANE CYCLIC TRIMER

[75] Inventor: Edwin R. Evans, Clifton Park, N.Y.

[73] Assignee: General Electric Company, Waterford, N.Y.

[21] Appl. No.: 427,295

[22] Filed: Apr. 21, 1995

[51] Int. Cl.$^6$ .................................................. C07F 7/08
[52] U.S. Cl. ................................................... 556/462
[58] Field of Search ........................................... 556/462

[56] References Cited

U.S. PATENT DOCUMENTS

| | | |
|---|---|---|
| 2,759,008 | 8/1956 | Dunham et al. .................. 556/462 |
| 3,274,154 | 9/1966 | Kendrick et al. .................. 556/462 X |
| 4,722,987 | 2/1988 | Ikeno et al. ...................... 556/462 X |
| 4,842,902 | 6/1989 | Brown et al. . |

*Primary Examiner*—Paul F. Shaver

[57] ABSTRACT

A method is provided for making a polyfluoroalkylsiloxane fluid in the form of a homopolymer, copolymer, or terpolymer, by polymerizing polyfluoroalkylsiloxane trimer in the presence of a mixture containing an effective amount of water and a strong acid catalyst, such as trifluoromethanesulfonic acid.

10 Claims, No Drawings

PROCESS FOR POLYMERIZING POLYFLUOROALKYLSILOXANE CYCLIC TRIMER

BACKGROUND OF THE INVENTION

The present invention relates to a method of ring opening cyclic diorganosiloxane comprising diorganosiloxy units having a polyfluoroalkyl radical attached to silicon by carbon-silicon bonds. More particularly, the present invention relates to the employment of water in combination with a strong acid catalyst, such as trifluoromethanesulfonic acid (triflic acid) to facilitate the polymerization of fluoroalkylsiloxane cyclic to provide fluoroalkylsiloxane homopolymer, copolymer and terpolymer fluids.

Ring opening polymerization of trifluoropropylmethylsiloxane cyclic trimer with trifluoromethanesulfonic acid has been described in Polymer Preprints, by G. Friends et al., Vol. 33, pages 493–494 August 1992, and Chang et al. Vol 33, pages 491–492. These publications, and Shintani et al, Japanese patent JPO 395,226, describe the formation of low viscosity fluoroalkylsiloxane copolymer fluids after long reaction times, such as 24 hours or more, at temperatures of 90° C. or greater. In addition, as shown by U.S. Pat. No. 4,842,902, fluoroalkylsiloxane copolymers can be prepared by reacting cyclic diorganosiloxane, such as 1,3-divinyltetramethyl, or hexamethyl cyclic trimer together with diorganosiloxane hydrolyzate having terminal diorganofluoroalkylsiloxane units.

It would be desirable therefor to provide a procedure for making polyfluoroalkylsiloxane fluids, for example, fluid homopolymers, copolymers, and terpolymers, by effecting the direct ring opening polymerization of polyfluoroalkylsiloxane cyclics.

It also would be desirable to convert polyfluoroalkylsiloxane cyclics to polyfluoroalkylsiloxane fluids having viscosities in the range of 300–40,000 centipoise at 25° C., while minimizing the formation of undesirable cyclics.

In addition, it would be desirable to make polyfluoroalkylsiloxane fluids at temperatures in the range of 20° C. to 120° C. within 4 to 10 hours.

SUMMARY OF THE INVENTION

The present invention is based on the discovery that polyfluoroalkylsiloxane fluids can be made by effecting the direct ring opening polymerization of a polyfluoroalkylsiloxane cyclic. It has been found that direct polyfluoroalkylsiloxane cyclic ring opening polymerization can be achieved if an effective amount of a strong acid is used in combination with a predetermined amount of water.

As used hereinafter, the term "polyfluoroalkylsiloxane cyclic" means a (3–8) cyclic polydiorganosiloxane having at least one diorganosiloxy unit with a polyfluoroalkyl radical attached to silicon by carbon-silicon bonds, where the diorganosiloxy units of the polyfluoroalkylsiloxane cyclic are members selected from the group consisting of polyfluoroalkylorganosiloxy, or $R(R^1)SiO_1$ units, and a mixture of $R(R^1)SiO_1$ units and diorganosiloxy, or $(R^1)_2SiO_1$ units, where R is a $C_{(3-8)}$ polyfluoroalkyl radical, and $R^1$ is a fluorine-free $C_{(1-13)}$ organo radical.

As used hereinafter, the term "polyfluoroalkylsiloxane fluid" means a polydiorganosiloxane having a viscosity in the range of 300–40,000 centipoise at 25° C. which comprise $R(R^1)SiO_1$ units as previously defined, where such units can be the same or different. Accordingly, polyfluoroalkylsiloxane fluid also includes homopolymer, copolymer and terpolymer. Polyfluoroalkylsiloxane fluid also can consist essentially of a mixture of $R(R^1)SiO_1$ units and $(R^1)_2SiO_1$ units, where R and $R^1$ are as previously defined.

STATEMENT OF THE INVENTION

There is provided by the present invention, a method for making polyfluoroalkylsiloxane fluid comprising, (i) effecting the ring opening polymerization of cyclic polydiorganosiloxane in the presence of a mixture comprising by weight, 0.02 to 0.1 part of water, and an effective amount of a strong acid catalyst having a $pK_a$ of at least 4.7, per 100 parts of polymerization mixture, where the cyclic polydiorganosiloxane consists essentially of a member selected from the group consisting of $R(R^1)SiO_1$ units, and a mixture of $R(R^1)SiO_1$ units and $(R^1)_2SiO_1$ units, where R and $R^1$ are as previously defined, (ii) treating the resulting mixture of (i) with a neutralizing agent, and (iii) recovering a polyfluoroalkylsiloxane fluid from the mixture of (ii).

DETAILED DESCRIPTION OF THE INVENTION

Polyfluoroalkyl radicals which are included within R above, are preferably $CF_3(CH_2)_2-$, and $C_4F_9CH_2CH_2-$. Organo radicals included within $R^1$ are for example $C_{(1-8)}$ alkyl radicals such as methyl, ethyl, propyl, isopropyl, butyl, and pentyl; alkenyl radicals such as vinyl, and propenyl; cycloalkyl such as cyclopentyl, and cyclohexyl; aryl such as phenyl, tolyl, xylyl, and naphthyl; haloaryl such as chlorophenyl.

Among the strong acid catalysts which can be used in the practice of the invention, there is preferably included trifluoromethanesulfonic acid, or Triflic acid. In addition, other materials having a pK in the range of 5.8 to 4.7, also can be used effectively as catalysts, such as $HClO_4$, $HOIOF_4$, HBr and HI. An effective amount of the strong acid catalyst is 0.02 to 0.20 part of catalyst, per 100 parts of cyclic polydiorganosiloxane polymerization mixture.

Some of the polyfluoroalkylsiloxane cyclics which can be used in the practice of the invention are preferably trifluoropropylmethylsiloxane cyclic trimer and nonafluorohexylmethylsiloxane cyclic trimer. In addition, other polyfluorosiloxane cyclic trimers which can be used are for example, $[F(CF_2)_6CH_2CH_2-Si-(CH_3)O]_3$ and $[F(CF_2)_8CH_2CH_2-Si-(CH_3)O]_3$. Although cyclic trimer is preferred, higher cyclics also can be used if desired such as the corresponding, tetramer and pentamer.

The polyfluoroalkylsiloxane cyclics can be polymerized to homopolymers which can have a viscosity of from 300 centipoise to 15,000 centipoise at 25° C.

Diorganosiloxane cyclic trimer, such as $[CH_2=CH-Si(CH_3)O]_3$, and the corresponding cyclic tetramer, which are free of chemically combined polyfluoroalkyl radicals, along with chain-stopping units, also can be used in combination with polyfluoroalkylsiloxane cyclic to produce a variety of copolymers and terpolymers if desired. Additional diorganosiloxane cyclics are for example hexamethylcyclotrisiloxane, and octamethylcyclotetrasiloxane. Chain-stoppers also can be used, such as a hexaorganodisiloxane, for example, hexamethyldisiloxane, tetramethyldisiloxane, and tetramethyl 1,3 divinyl disiloxane.

The polyfluoroalkylsiloxane copolymers, and terpolymers having chemically combined diorganosiloxane units free of polyfluoroalkyl radicals, preferably have from about 10 mole percent to about 80 mole percent of diorganosiloxane units which have at least one polyfluoroalkyl radicals based on the total moles of diorganosiloxane units in the polydiorganosiloxane.

The polyfluoroalkylsiloxane polymers made in accordance with the practice of the invention, can have a molecular weight in the range of about 2000 to about 24,000 and a viscosity of from about 200 centipoise to about 20,000 centipoise at 25° C.

Some of the applications in which the polyfluoroalkylsiloxane polymers made in accordance with the present invention can be used, are for example, mechanical pump fluids, bearing lubricants, and hydrocarbon oil anti-foam agents.

In the practice of the preferred form of the invention, the order of addition of the various ingredients is not critical. However, it is preferred to add increments of water within the previously defined proportions to the polyfluoroalkylsiloxane cyclic. For purposes of more clearly defining the invention, the term polyfluoroalkylsiloxane cyclic is intended to include the polyfluoroalkylsiloxane cyclic monomer, a mixture of polyfluoroalkylsiloxane cyclic monomers; a mixture of polyfluoroalkylsiloxane cyclic monomer, or cyclic monomers, and diorganosiloxane cyclic consisting essentially of $(R^1)_2SiO_1$ units, where $R^1$ is as previously defined is also included. It is also preferred to add the water to the polyfluoroalkylsiloxane cyclic while the latter is stirring and after the polyfluoroalkylsiloxane cyclic has been initially dried.

After addition of the water, the acid catalyst can be added to the mixture while it is being agitated. It has been found that after the addition of the catalyst, an exotherm can occur resulting in a rise in temperature. External heat can be applied if desired resulting in an overall temperature during the reaction of about 20° C. to about 130° C. Reaction time of 4 hours to 12 hours is not unusual depending upon such factors as temperature and reactants.

Upon termination of the reaction as shown by the formation of a polyfluoroalkylsiloxane fluid within a desired viscosity range, the fluid can be a stabilized by adding an effective of a base to substantially neutralize the mixture. Bases which can be used are for example alkaline earth carbonates and oxides, magnesium carbonate, magnesium oxide such as barium carbonate, and magnesium carbonate; alkali metal bicarbonates such as sodium bicarbonate and ammonium bicarbonate. In addition, organosilazanes such as hexamethyldisilazane can be used. It is preferred to remove any excess base prior to the recovery of the polyfluoroalkylsiloxane fluid. Filtration has been found useful to provide removal of the alkaline earth carbonates, while stripping has been found effective for removing organosilazane.

In order to more fully understand the practice of the present invention, the following examples are given by way of illustration and not by way of limitation. All parts are by weight unless otherwise indicated.

EXAMPLE 1

There was added 3.7 g of water followed by 1.3 g of trifluoromethanesulfonic acid (triflic acid) to a mixture of 1100 g of trifluoropropylmethylsiloxane cyclic trimer (previously dried over silica) and 131.0 of divinyltetramethyldisiloxane. The mixture acquired a light amber color and displayed an exotherm of 12° C. The temperature of the mixture rose from 28° to 40° C. over a period of 40 minutes. The temperature of the mixture was raised and maintained at 90° C. for 6 hours. The mixture was allowed to cool and neutralized twice with 10 g of sodium bicarbonate. It was then filtered through Celite 545. There was obtained 1166.9 g of a clear colorless fluid. The material was vacuum stripped to provide 938 g of a fluid having a volatiles content of 2.4% of 400 centipoise at 25° C. The fluid was found to have a specific gravity of 1.2514 at 25° C. and a vinyl content of 1.45 wt %. Based on method of preparation and its vinyl content, the fluid was a polytrifluoropropylmethylsiloxane homopolymer having an average of 23 trifluoropropylmethylsiloxy units and terminal vinyldimethylsiloxy units. It was useful as a base polymer for addition cured fluorosilicone gels.

EXAMPLE 2

There was added 0.3 g of water and 0.3 g of triflic acid to a mixture while it was stirring of 400g of trifluoropropylmethylsiloxane cyclic trimer, 200 g of nonafluorohexylmethylsiloxane cyclic trimer and 18g of divinyltetramethyldisiloxane. The temperature of the mixture rose slowly from 29° C. to 40° C. The reaction mixture was heated to 112° C. for 1.5 hours. The mixture was then treated with 11.1 g of magnesium carbonate for 3 hours and then pressure filtered through Celite 545. There was obtained 739.5 g of a clear colorless fluid. The fluid was stripped to provide 614 g (76.3% yield) of a fluid having a specific gravity of 1.3548 at 25° C. Its viscosity was 860 and its vinyl content was 0.77 wt %. Based on method of preparation and vinyl content, the fluid was a copolymer having an average of 20 trifluoropropylmethylsiloxy units and 12 nonafluorohexylmethylsiloxy units. Its refractive index was 1.37 at 25° C. It was useful as a base polymer for fluorosilicone grade curable plasticizer.

EXAMPLE 3

There was added 18 g of divinyltetramethyldisiloxane and 0.2 g of water to a mixture while it was stirring of 400 g of trifluoropropylmethylsiloxane cyclic trimer and 200 g of nonafluorohexylmethylsiloxane cyclic trimer and 1 g of methylvinylsiloxane cyclic trimer. While the mixture was agitated at 26° C., 0.18cc, or 0.309g of triflic was added. The reaction temperature rose to 40° C. over a 55 minute interval. The mixture was heated to 116° C. for 21/4 hours. There was added 11g of magnesium carbonate over a period of 4 hours at RT. There was obtained 496g (80% yield) of a colorless fluid after pressure filtration through Celite 545. There was obtained a fluid having a viscosity of 1,340 centipoise at 23° C., a vinyl content of 0.76 %, a specific gravity of 1.3480 (23° C.) and a refractive index of 1.3725 (23° C.). Based on method of preparation, the fluid was a terpolymer having terminal vinyldimethylsiloxy units and consisting essentially of chemically combined trifluoropropylmethylsiloxy units, nonafluorohexylmethylsiloxy units and methylvinylsiloxy units. It was useful as a plasticizer for fluorosilicone rubber compounds.

EXAMPLE 4

There were added 35g of hexamethyldisiloxane and 0.5g of water to 1000g of a fluorosilicone cyclic trimer while it was stirring which had 0.37 wt % of $[CF_2=CH-CH_2-Si-(CH_3)O]$—units. While the resulting mixture was stirring, there was added 0.3 cc (0.5g) of triflic acid. The mixture was then heated to 31.5° C. and the temperature rose to 48° C. after 25 minutes. The mixture was then heated and maintained at a temperature of 100°–124° C. for 3 hours. The mixture was then cooled to 60° C. and 11.0 g of BaCO$_3$ were added. The mixture was then stirred for 2 hours and then filtered through Celite 545 to provide 942 g of a clear colorless fluid. The fluid was vacuumed stripped at 225° C./1 torr to provide 785 g of material having a 1.4% volatiles content, a viscosity of 1070 centipoise (25° C.) and a specific gravity 1.276 (25° C.). Based on FTIR analysis, the product was a fluorosilicone polymer having 0.33 wt % of $CF_2$=CH—$CH_2$—unsaturation (1748 cm$^{-1}$).

EXAMPLE 5

There was added 0.33cc of triflic acid to a stirred mixture of 500 g of trifluoropropylmethylsiloxane cyclic trimer, about 18 g of tetramethyldisiloxane and 0.5 g of water. The temperature of the mixture rose from 25° C. to 45° C. over a period of 30 minutes. After an additional 10 minutes, the mixture was heated and maintained at a temperature of 115° C. for three hours. The mixture was allowed to cool to 25° C. and 11.0 g of MgCO$_3$ were added. There was obtained, 592 g of product having a viscosity of 16 centipoise at 25° C. and a specific gravity of 1.1144 after the mixture was filtered through Celite 545 and stripped at 140° C. Based on method of preparation and FTIR analysis, the product was a fluorosilicone fluid having an Si—H content of 0.29%.

What is claimed is:

1. A method for making polyfluoroalkylsiloxane fluid consisting essentially of,
   (i) effecting the ring opening polymerization of cyclic polydiorganosiloxane in the presence of a mixture comprising by weight, 0.02 to 0.1 part of water, and an effective amount of a strong acid catalyst having a p$K_a$ of at least 4.7, per 100 parts of polymerization mixture, where the cyclic polydiorganosiloxane consists essentially of a member selected from the group consisting of R(R$^1$)SiO$_1$ units, and a mixture of R(R$^1$)SiO$_1$ units and (R$^1$)$_2$SiO$_1$ units, where R is a C$_{(3-8)}$ polyfluoroalkyl radical, and R$^1$ is a fluorine free C$_{(1-13)}$ organo radical,
   (ii) treating the resulting mixture of (i) with a neutralizing agent selected from the group consisting of alkaline earth carbonates, alkaline earth oxides, and alkalimetalbicarbonates, and
   (iii) recovering a polyfluoroalkylsiloxane fluid from the mixture of (ii).

2. A method in accordance with claim 1, where the strong acid is trifluoromethanesulfonic acid.

3. A method in accordance with claim 1, where the cyclic polydiorganosiloxane has at least one trifluoropropylmethylsiloxy unit.

4. A method in accordance with claim 1, where the cyclic polydiorganosiloxane has at least one nonafluorohexylmethylsiloxy unit.

5. A method in accordance with claim 1, where the cyclic polydiorganosiloxane is a mixture of a trifluoropropylmethylsiloxane cyclic trimer, and a nonafluorohexylmethylsiloxane cyclic trimer.

6. A method in accordance with claim 1, where the neutralizing agent is an alkaline earth carbonate.

7. A method in accordance with claim 1, where the cyclic polydiorganosiloxane is an organo siloxane homopolymer.

8. A method in accordance with claim 7, where the organosiloxane homopolymer is hexamethyl disiloxane.

9. A method in accordance with claim 1, where the polyfluoroalkylsiloxane fluid is a polyfluoroalkylsiloxane copolymer.

10. A method in accordance with claim 1, where the polyfluoroalkylsiloxane fluid is a polyfluoroalkylsiloxane terpolymer.

* * * * *